United States Patent [19]

Robertson

[11] Patent Number: 4,617,302

[45] Date of Patent: Oct. 14, 1986

[54] INOTROPIC AGENTS

[75] Inventor: David W. Robertson, Indianapolis, Ind.

[73] Assignee: Eli Lilly and Company, Indianapolis, Ind.

[21] Appl. No.: 660,836

[22] Filed: Oct. 15, 1984

[51] Int. Cl.$^4$ ............... C07D 401/10; C07D 403/10; A61K 31/50; A61K 31/55

[52] U.S. Cl. ................... 514/254; 544/230; 514/217; 546/18; 540/523; 540/543

[58] Field of Search ............... 544/238, 230; 260/243.3; 514/217

[56] References Cited

U.S. PATENT DOCUMENTS

| | | | |
|---|---|---|---|
| 3,845,050 | 10/1974 | Lebkuecher et al. | 260/250 A |
| 4,258,185 | 3/1981 | Nakao et al. | 544/114 |
| 4,304,777 | 12/1981 | Lesher et al. | 424/250 |
| 4,353,905 | 10/1982 | Sircar et al. | 424/250 |
| 4,361,563 | 11/1982 | Austel et al. | 424/250 |
| 4,397,854 | 8/1983 | Sircar | 424/250 |
| 4,404,203 | 9/1983 | Sircar | 424/250 |

FOREIGN PATENT DOCUMENTS

| | | |
|---|---|---|
| 68310 | 1/1983 | European Pat. Off. . |
| 2031404 | 4/1980 | United Kingdom . |

OTHER PUBLICATIONS

Curran et al., J. Med. Chem., 17(3), 273 (1974).
McEvoy et al., J. Med. Chem., 17(3), 281 (1974).
Derwent 27593K/12 abstracting German OLS No. 3,135,617.
Derwent 18918K/08 abstracting Japanese Patent No. J58008016.
Nakao Chemical Abstracts 93:46702d (1980).
Aghalyan Chemical Abstracts 91:140700g (1979).
M.T.C., Inc. Chemical Abstracts 101:90957y (1984).
Japanese Abstract of Japan Patent Publication No. 58-8016.

Primary Examiner—Mark L. Berch
Attorney, Agent, or Firm—Robert A. Conrad

[57] ABSTRACT

This invention provides certain pyridazinone derivatives, their pharmaceutical formulations, and their use as positive inotropic agents.

20 Claims, No Drawings

INOTROPIC AGENTS

BACKGROUND OF THE INVENTION

The cardiac glycosides and the sympathomimetic amines are the principal inotropic agents used in the management of congestive heart failure. Although the cardiac glycosides, especially digitalis, are among the most frequently prescribed drugs, they have numerous liabilities such as a low therapeutic index and erratic absorption, and are associated with life-threatening arrhythmias and deleterious drug-drug interactions. In addition, many patients either do not respond, or become refractory to these agents. The sympathomimetic amines, such as dopamine and epinephrine, have limited utility due to positive chronotropic effects, arrhythmogenic properties, and oral ineffectiveness.

More recently, new classes of inotropic agents have been found. These include certain dihydropyridazinone derivatives such as those taught in U.S. Pat. Nos. 4,353,905, 4,361,563, 4,304,777, and 4,404,203 which cause an increase in myocardial contractility in anesthetized dogs and cats. Other pyridazinone derivatives are taught in the art to be cardiotonics, antihypertensives, and antithrombotic agents; see, e.g., U.S. Pat. No. 4,258,185.

The present invention provides certain pyridazinone derivatives which are potent, long-acting, orally effective positive inotropic agents which cause minimal effects on blood pressure and heart rate.

SUMMARY OF THE INVENTION

This invention provides compounds of the formula

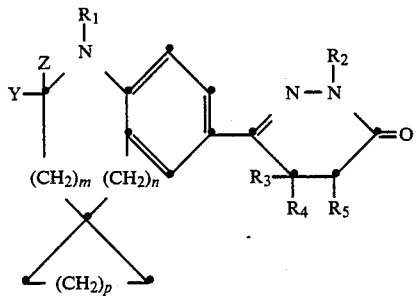

wherein
Y and Z are each hydrogen, or when taken together are =O;
$R_1$, $R_2$, $R_3$, $R_4$, and $R_5$ are independently hydrogen or $C_1$–$C_4$ alkyl, or $R_5$ and one of $R_3$ and $R_4$ taken together form a bond;
m and n are independently 0, 1 or 2, provided that (m+n) is no greater than 2; and
p is 0, 1 or 2, and pharmaceutically acceptable acid addition salts thereof.

This invention also provides a method of treating a mammal, including a human subject, suffering from or susceptible to heart failure, which comprises administering to said mammal an effective amount of a compound of the above formula.

According to a further aspect of the present invention, there are provided pharmaceutical formulations which comprise as active ingredient a compound of Formula I in association with a pharmaceutically acceptable carrier, diluent, or excipient therefor.

DETAILED DESCRIPTION AND PREFERRED EMBODIMENTS

The term "$C_1$–$C_4$ alkyl" when used herein refers to the straight and branched aliphatic radicals of one to four carbon atoms, and includes methyl, ethyl, propyl, isopropyl, butyl, isobutyl, sec-butyl, and tert-butyl.

A preferred group of compounds are those of the above formula wherein (a) Y and Z taken together are =O;
(b) each of $R_1$, $R_2$, $R_5$, and one of $R_3$ and $R_4$ is hydrogen;
(c) the other of $R_3$ and $R_4$ is hydrogen or methyl;
(d) m and n are each 0; and
(e) p is 0.

Especially preferred are 5'-(1,4,5,6-tetrahydro-6-oxo3-pyridazinyl)spiro(cyclopropane-1,3'-[3H]indol)-2'(1'H)-one and 5'-(1,4,5,6-tetrahydro-4-methyl-6-oxo-3-pyridazinyl)spiro(cyclopropane-1,3'[3H]indol)-2'(1'H)-one, and the pharmaceutically acceptable salts thereof.

The term "$C_1$–$C_4$ alkyl" when used herein refers to the straight and branched aliphatic radicals of one to four carbon atoms, and includes methyl, ethyl, propyl, isopropyl, butyl, isobutyl, sec-butyl, and tert-butyl.

The compounds of the present invention can be prepared by any of several methods known to those skilled in the art. In addition to their utility as inotropic agents, some of the compounds of the present invention are also useful as intermediates to other compounds of the invention. For example, compounds where $R_1$ is hydrogen may be alkylated to provide the corresponding compounds of this invention wherein $R_1$ is $C_1$–$C_4$ alkyl according to standard methods well known in the art. Similarly, the carbonyl derivatives of Formula I (Y and Z taken together are =O) may be reduced to the methylene compounds (Y and Z are each hydrogen) by standard reductive techniques known in the art.

A typical synthesis of compounds of the invention is depicted in Scheme I.

Scheme I

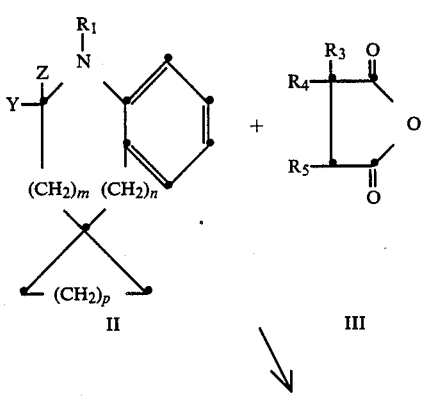

-continued
Scheme I

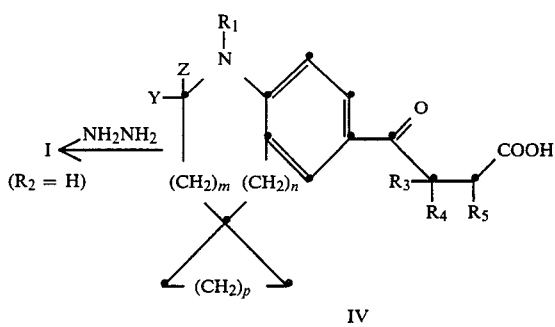

IV

As summarized in Scheme I, a preferred method of making the compounds of Formula I wherein $R_2$ is hydrogen comprises reacting the appropriate phenyl derivative II with a maleic or succinic anhydride derivative III, in the presence of a Lewis acid such as aluminum chloride, and in the presence of a nonreactive solvent, for example a halogenated alkane such as 1,1,2,2-tetrachloroethane, a dialkylformamide such as dimethylformamide, or the like. This reaction is a standard Friedel-Crafts acylation reaction and is generally complete within about 24 hours when carried out at a temperature from about 25° C. up to the reflux temperature of the reaction mixture, for example about 150° C. This reaction provides the corresponding gamma-ketoacid IV, which can be reacted with hydrazine or hydrazine hydrate in the absence of a solvent, or if preferred in the presence of an inert solvent such as water, an alcohol such as ethanol, tetrahydrofuran, toluene, dimethylformamide, or the like, at a temperature ranging from about 20° C. to the reflux temperature of the reaction mixture. The compounds thus formed are compounds of Formula I wherein $R_2$ is hydrogen, which may be further transformed to other compounds of Formula I by methods as previously described.

When intermediate III is unsymmetrical, two possible products from the acylation are possible. In such cases, acylation of II with intermediate V

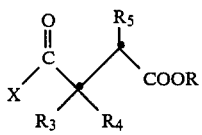

V where X is bromo or chloro and R is, for example, $C_1$–$C_4$ alkyl, preferably methyl or ethyl, under standard acylation conditions, gives the ester derivative of intermediate IV which can be transformed into I ($R_3$=H) in the same way as previously described.

In addition, other methods of transforming II into IV are generally taught in U.S. Pat. No. 4,258,185.

Intermediates II, III, and V and other required reagents are commercially available, are known in the literature, or can be prepared by methods known in the literature or by the methods described in the following examples.

Depending upon the definitions of $R_3$, $R_4$, and $R_5$, the compounds of Formula I may exist as stereo-isomers. This invention is not limited to any particular isomer but includes all possible individual isomers and racemates of the compounds of Formula I.

The pharmaceutically acceptable acid addition salts of this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, and the like. Typical pharmaceutically acceptable salts of the invention thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

The following examples further illustrate the preparation of the compounds of this invention. The examples are illustrative only and are not intended to limit the scope of the invention in any way.

EXAMPLE 1

5'-(1,4,5,6-tetrahydro-6-oxo-3-pyridazinyl)-spiro[cyclopropane-1,3'-[3H]indol]-2'(1'H)-one A. Preparation of 1'-(2-bromoethyl)spiro[cyclopropane-1,3'-[3H]indol]-2'(1'H)-one.

To a slurry of 46.0 g of 60% sodium hydride in oil in 1 liter of dimethylformamide was added a solution of 50.0 g of oxindole in 1.5 liters of dimethylformamide. After hydrogen evolution ceased, the reaction was cooled to 4° C. and a solution of 132.8 ml of 1,2-dibromoethane in 500 ml of dimethylformamide was quickly added. The reaction was stirred for 1 hour at 15° C. followed by 12 hours of stirring at room temperature. The reaction mixture was concentrated in vacuo. The residue was treated with water and extracted with ethyl acetate. The organic extract was washed with water and a saturated sodium chloride solution, dried over magnesium sulfate, and concentrated in vacuo to provide 98 grams of a dark oil. Chromatography over silica gel provided 14.8 g of a yellow oil which was identified as the subtitle intermediate by nuclear magnetic resonance and mass spectrosopy.

B. Preparation of spiro[cyclopropane-1,3'-[3H]indol]-2'(1'H)-one.

A solution of 14.0 g of 1'-(2-bromoethyl)-spiro[cyclopropane-1,3'-[3H]indol]-2'(1'H)-one in 150 ml of anhydrous tetrahydrofuran was added dropwise to 12.8 g of anhydrous magnesium metal. A few milliliters of 1,2-dibromoethane were added to initiate the reaction and gas evolution became evident. After the addition was complete, the solution was refluxed for 18 hours. The solution was cooled to room temperature, filtered, and evaporated in vacuo. The residue was treated with 1N hydrochloric acid and extracted first with methylene chloride and then with ethyl acetate. The combined organic extracts were washed with a saturated sodium chloride solution, dried over magnesium sulfate, and evaporated to dryness. The residue was chromatographed over silica gel to provide 3.64 g of the desired subtitle intermediate, m.p. 182°–184° C.

Analysis for $C_{10}H_9NO$: Calculated: C, 75.45; H, 5.70; N, 8.80; Found: C, 75.67; H, 5.60; N, 9.08.

C. Preparation of 1',2'-dihydro-γ,2'-dioxospiro[cyclopropane-1,3'-[3H]indole]-5-butanoic acid.

To 4.2 grams of anhydrous aluminum chloride were added 0.69 ml of dimethylformamide. To this slurry were added a mixture of 0.32 g of succinic anhydride and 0.5 g of spiro[cyclopropane-1,3'-[3H]indol]-2'(1'H)-one. The mixture was stirred for 3.5 hours at 80° C. The reaction mixture was poured into a mixture of 100 ml of ice and 25 ml of concentrated hydrochloric acid. After cooling overnight, the resulting precipitate was recovered by filtration. Crystallization from dimethylformamide/water provided the title product in 57.4% yield, m.p. 256°–257° C.

Analysis for $C_{14}H_{13}NO_4$: Calculated: C, 64.86; H, 5.05; N, 5.40; Found: C, 64.74; H, 5.05; N, 5.65.

D. Preparation of 5'-(1,4,5,6-tetrahydro-6-oxo-3-pyridazinyl)spiro[cyclopropane-1,3'-[3H]indol]2'(1'H)-one.

A slurry of 0.35 grams of 1',2'-dihydroγ,2'-dioxospiro[cyclopropane-1,3'-[3H]indole]-5-butanoic acid in 25 ml of absolute ethanol was treated with 0.17 ml of 85% hydrazine hydrate. The reaction was heated at reflux for 4 hours. After cooling, the resulting precipitate was filtered and recrystallized from dimethylformamide/water to provide the desired title product in 64.9% yield, m.p. >300° C. Analytical HPLC indicated the product was more than 99% pure. The mass spectrum and $^1$H-NMR were consistent with the assigned structure.

Analysis for $C_{14}H_{13}N_3O_2$: Calculated: C, 65.87; H, 5.13; N, 16.46; Found: C, 63.66; H, 5.27; N, 15.86.

EXAMPLE 2

5'-(1,4,5,6-tetrahydro-6-oxo-3-pyridazinyl)-spiro[cyclopentane-1,3'-[3H]indol]-2'(1'H)-one A. Preparation of cyclopentanecarboxylic acid, 2-phenylhydrazide.

A solution of 46.08 g of cyclopentanecarboxylic acid chloride in 200 ml of anhydrous ether was added to a 0° C. solution of 68.4 ml of phenylhydrazine in 200 ml of anhydrous ether over a 1 hour period. The reaction was stirred an additional 1 hour and diluted with water. The layers were separated and the aqueous layer was extracted with ethyl acetate. The combined organic extracts were washed sequentially with 1N hydrochloric acid, water, a saturated sodium bicarbonate solution, water, and a saturated sodium chloride solution, dried over sodium sulfate, and concentrated in vacuo. Recrystallization of the residue from ethyl acetate/hexane provided 55.9 g of the desired subtitle intermediate as a white powder, m.p. 138°–139° C.

B. Preparation of spiro[cyclopentane-1,3'-[3H]indol]-2'(1'H)-one.

A mixture a 5.0 g of cyclopentanecarboxylic acid, 2-phenylhydrazide and 1.64 g of calcium hydride was heated gradually to 240° C. over a 2.5 hour period. After heating at 240° C. for an additional 30 minutes, the mixture was cooled to room temperature. A solution of 20 ml of water and 50 ml of methanol was added dropwise to the residue. The resulting slurry was brought to pH 1 with concentrated hydrochloric acid, diluted with 50 ml of water, and brought to reflux for 20 minutes. The solution was cooled and brought to pH 3. The resulting precipitate was filtered and recrystallized from ethyl acetate/hexane to provide 1.3 g of the desired subtitle intermediate, m.p. 110°–111° C.

Analysis for $C_{12}H_{13}NO$: Calculated: C, 76.98; H, 7.00; N, 7.48; Found: C, 76.69; H, 7.07; N, 7.24.

C. Preparation of 1',2'-dihydro-γ,2'-dioxospiro[cyclopentane-1,3'-[3H]indole]-5-butanoic acid.

The title intermediate was prepared from spiro[cyclopentane-1,3'-[3H]indol]-2'(1'H)-one in 24.9% yield following the procedure of Example 1C. The intermediate had a melting point of 160° C. with decomposition.

D. Preparation of 5'-(1,4,5,6-tetrahydro-6-oxo-3-pyridazinyl)spiro[cyclopentane-1,3'-[3H]indol]-2'(1'H)-one.

The title product was prepared from the intermediate of Example 2C in 37.3% yield following the procedure of Example b 1D. The title product had a melting point of >300° C.

Analysis for $C_{16}H_{17}N_3O_2$: Calculated: C, 67.83; H, 6.05; N, 14.83; Found: C, 67.78; H, 5.90; N, 14.54.

EXAMPLE 3

5'-(1,4,5,6-tetrahydro-6-oxo-3-pyridazinyl)-spiro[cyclobutane-1,3'-[3H]indol]-2'(1'H)-one The title product was prepared following the general procedures of Example 2. The cyclobutanecarboxylic acid, 2-phenylhydrazide was prepared from the acid chloride in 66.4% yield, m.p. 140°–145° C. spiro[cyclobutane-1,3'-[3H]indol]-2'(1'H)-one was prepared in 9% yield from the hydrazide intermediate, m.p. 122°–123° C. The intermediate 1',2'-2-dihydro-γ,2'-dioxospiro[cyclobutane-1,3'-[3H]indole]-5-butanoic acid was prepared from the non-acylated intermediate in 34% yield. The title product was prepared from the γ-ketobutanoic acid derivative in 51.9% yield following the procedures of Examples 1D and 2D. The title product had a melting point of >300° C.

Analysis for $C_{15}H_{15}N_3O_2$: Calculated: C, 66.90; H, 5.61; N, 15.60; Found: C, 67.11; H, 5.40; N, 15.41.

EXAMPLE 4

5'-(1,4,5,6-tetrahydro-4-methyl-6-oxo-3-pyridazinyl)-spiro[cyclopropane-1,3'-[3H]indol]-2'(1'H)-one A. Preparation of 5'-(1-oxopropyl)spiro-[cyclopropane-1,3'-[3H]indol]-2'(1'H)-one A slurry was made from 7.5 ml of dimethylformamide and 45.5 g of anhydrous aluminum chloride. The temperature rose to 40° C. and 2.97 ml of propionyl chloride and 5.43 g of spiro[cyclopropane-1,3'-[3H]indol]-2'(1'H)-one were added. The mixture was stirred for 2 hours at 70° C. and was slowly poured into a mixture of ice and 50 ml of concentrated hydrochloric acid. After cooling overnight, the resulting precipitate was recovered by filtration. Crystallization from ethyl acetate provided 4.9 grams of the desired subtitle intermediate, m.p. 183°–185° C.

Analysis for $C_{13}H_{13}NO_2$: Calculated: C, 72.54; H, 6.09; N, 6.51; Found: C, 72.47; H, 6.14; N, 6.42.

B. Preparation of 1',2'-dihydro-N,N,N,β-tetramethyl-γ,2'-dioxospiro[cyclopropane-1,3'-[3H]indole]-5'-propanaminium iodide.

A mixture of 3.56 g of dimethylamine hydrochloride, 2.84 ml of 37% formaldehyde, 17.6 ml of acetic anhydride, and 6.25 g of 5'-(1-oxopropyl)spiro[cyclopropane-1,3'-[3H]indol]-2'(1'H)-one was heated at 90° for two hours and then stirred overnight at room temperature. The reaction was concentrated in vacuo and the residue was boiled in acetone for 10 minutes. The acetone was decanted and the residue was dissolved in water. The solution was extracted with ethyl acetate. The aqueous portion was basified to pH 8 with 5N sodium hydroxide and extracted with ethyl acetate. This organic extract was washed with a saturated sodium chloride solution, dried over sodium sulfate, and concentrated in vacuo. The resulting oil was dissolved in acetone and 3.4 ml of methyl iodide were added. The reaction was stirred overnight at room temperature and the resulting precipitate was filtered to provide 4.44 g of the desired subtitle intermediate, m.p. 163°–170° C.

Analysis for $C_{17}H_{23}IN_2O_2$: Calculated: C, 49.29; H, 5.60; N, 6.76; Found: C, 49.48; H, 5.83; N, 6.62.

C. Preparation of 1',2'-dihydro-β-methyl-γ,2'-dioxospiro[cyclopropane-1,3'-[3H]indole]-5'butanenitrile.

To a solution of 4.44 g of the quaternary salt of Example 4B above in 100 ml of methanol was added a solution of 1.7 g of potassium cyanide in 50 ml of water. The reaction was stirred overnight at room temperature, diluted with water, and extracted with ethyl acetate. The organic extract was washed with water and a saturated sodium chloride solution, dried over sodium sulfate, filtered and evaporated to dryness. Chromatography of the residue over silica gel eluting with ethyl acetate/hexanes provided 2.4 g of the desired title intermediate, m.p. 143°–146° C.

Analysis for $C_{15}H_{14}N_2O_2$: Calculated: C, 70.85; H, 5.55; N, 11.02; Found: C, 70.74; H, 5.62; N, 10.92.

D. Preparation of 1',2'-dihydro-β-methyl-γ,2'-dioxospiro[cyclopropane-1,3'-[3H]indole]-5'-butanoic acid.

The 2.4 g of the nitrile from Example 4C above was slurried in 30 ml of 6N hydrochloric acid and heated to reflux for 2 hours. The reaction mixture was diluted with 200 ml of water and the resulting precipitate was recovered by filtration to provide 1.68 g of the desired subtitle intermediate as a yellow powder, m.p. 161°–162° C. The proton NMR and mass spectral data were consistent with the assigned structure.

E. Preparation of 5'-(1,4,5,6-tetrahydro-4-methyl-6-oxo-3-pyridazinyl)spiro[cyclopropane-1,3'-[3H]indol]-2'(1'H)-one.

Following the procedure of Example 1D, 1.65 g of the carboxylic acid of Example 4D above was treated with 0.78 ml of hydrazine hydrate to provide 1.05 g of the desired title product, m.p. 291°–293° C.

Analysis for $C_{15}H_{15}N_3O_2$: Calculated: C, 66.90; H, 5.61; N, 15.60; Found: C, 67.06; H, 5.71; N, 15.36.

The following compounds can be prepared according to the syntheses described in the above examples or by other methods generally known in the art.

1',4'-dihydro-6'-(1,4,5,6-tetrahydro-4-methyl-6-oxo-3-pyridazinyl)spiro[cyclopropane-1,3'(2'H)quinolin]-2'-one, 1',2'-dihydro-5'-(1,4,5,6-tetrahydro-4,4-diethyl-6-oxo-3-pyridazinyl)spiro[cyclopentane-1,3'-[3H]indole], 2',3'-dihydro-6'-(1,4,5,6-tetrahydro-4,5-dimethyl-6-oxo-3-pyridazinyl)spiro[cyclobutane1,4'(1'H)-quinoline], 4,5-dihydro-7-(1,4,5,6-tetrahydro-6-oxo-3-pyridazinyl)spiro[3H-1-benzazepine-3,1'-cyclopropan]-2(1H)-one, 1-ethyl-3,4-dihydro-7-(1,4,5,6-tetrahydro-1,4-dimethyl-4-ethyl-6-oxo-3-pyridazinyl)spiro[5H-1-benzazepine-5,1'-cyclobutan]-2(1H)-one, 1,2,3,5-tetrahydro-7-(1,6-dihydro-1-butyl-4-isopropyl-6-oxo-3-pyridazinyl)-spiro[4H-1-benzazepine-4,1'-cyclopentane], 1',4'-dihydro-6'-(1,4,5,6-tetrahydro-1,4,4,5-tetramethyl-6-oxo-3-pyridazinyl)spiro[cyclobutan-1,3'(2'H)-quinoline], 1,2,4,5-tetrahydro-7-(1,4,5,6-tetrahydro-6-oxo-3-pyridazinyl)spiro[3H-1-benzazepine-3,1'-cyclopentane], 1,5-dihydro-7-(1,6-dihydro-4-butyl-1-isopropyl-6-oxo-3-pyridazinyl)spiro[4H-1-benzazepine-4,1'-cyclobutane]-2(3H)-one, 1,2,3,4-tetrahydro-7-(1,6-dihydro-1-ethyl-6-oxo-3-pyridazinyl)spiro[5H-1-benzazepine-5,1'-cyclobutane], 1'-isopropyl-2',3'-dihydro-6'-(1,4,5,6-tetrahydro-5-methyl-6-oxo-3-pyridazinyl)spiro[cyclopropane-1,4'(1'H)-quinolin]-2'-one, The compounds of Formula I are particularly useful as inotropic agents due to their potency, long action of effect, and oral efficacy and are therefore useful in the treatment and prevention of heart failure. For example, the compounds of Formula I were examined as to their pharmacodynamic effects on the following test systems.

Positive Inotropic Activity in Isolated Cat Papillary Muscles

Cats of either sex were anesthetized with Metofane (1,1-difluoro-2,2-dichloroethyl methyl ether, Pittman-Moore). Their hearts were immediately removed and the papillary muscles dissected and suspended in individual organ baths. A platinum hook secured one end of the muscle to an electrode mounted in the bottom of the bath, and a silk thread attached the tendon to a Statham isometric transducer. The baths contained Krebs-Henseleit solution (36° C., bubbled with 95 percent oxygen - 5 percent carbon dioxide) of the following millimolar composition: NaCl, 118; KCl, 4.5; $CaCl_2$, 2.5; $KH_2PO_4$, 1.1; $MgSO_4$, 1.2; $NaHCO_3$, 25; and glucose, 11.

A base-line tension of 1.5 g was applied to each muscle. Square-wave pulses (5.0 msec. in duration, three times threshold voltage) delivered through the hook electrode and a second electrode positioned near the top of the muscle evoked 12 contractions/minute, which were recorded on a Grass polygraph. After the muscles had equilibrated for 60 minutes, the recorder gain was adjusted so that the pen deflected 10 mm. The test compound was introduced in a solution of normal saline in an amount to bring the final concentration of the compound to $10^{-5}$ or $10^{-4}$ molar. Increases in contractility were tabulated as millimeters of pen deflection in excess of the baseline value. In each experiment the maximum contractility was measured. Test results are summarized in Table I and are expressed as percent of control (control=100 percent). Values are the average of results from 2 to 8 muscles.

TABLE I

| Compound of Example | Effects of Compounds on Contractility in Cat Papillary Muscles | |
|---|---|---|
| | Contractility of Papillary Muscle* | |
| | Compound Concentration | |
| | $10^{-5}$ M | $10^{-4}$ M |
| 2 | 132 | 134 |
| 3 | 138 | 132 |

*Data are peak responses at the indicated concentration of compound and are expressed as a percent of control (control = 100 percent).

Experiments in Anesthetized Dogs

Mongrel dogs of either sex ranging in weight from 7 to 14 kg were used. Anesthesia was induced with sodium pentobarbital (30 mg/kg, i.v.) and maintained with supplemental doses as required. A positive-pressure pump was used to ventilate the dogs through an endotracheal tube (18 strokes/minute, 20 ml/kg stroke$^{-1}$), and a heating pad kept the body temperature at 37°-38° C.

Femoral arterial blood pressure was measured through a polyethylene catheter filled with heparin solution (16 units/ml) and connected to a Statham pressure transducer. A strain-gauge arch sutured to the right ventricle of the heart measured cardiac contractility. Tension on the gauge was adjusted to 50 g and the gain of the recorder (Beckman dynograph) was set so that 50 g caused a 10-mm pen deflection. Cardiac contractile tension was measured as millimeters of pen deflection or grams of tension. The test compounds were administered as an i.v. bolus (2-5 ml) in a normal saline vehicle following a 30-45 minute equilibrium period. In a control experiment, rapid intravenous injection of 50 ml of 5 percent dextran and mechanical compression of the aorta showed that the contractility measurements were independent of changes in preload and afterload. Heart rate was derived by means of a cardiotach which was triggered by the arterial pressure pulse signal and displayed on the polygraph. The maximum effects on contractility at various dose levels were determined and plotted and the dose required to produce a 50% increase in contractility (ED$_{50}$) was determined by interpolation. The ED$_{50}$'s for each compound tested are summarized in Table II.

TABLE II

Effects of Compounds on Ventricular Contractility in the Anesthetized dog

| Compound of Example | ED$_{50}$ (mcg/kg)* |
|---|---|
| 1 | 1.9 |
| 2 | 70 |
| 3 | 25 |

*i.v. dose required to produce a peak increase in contractility of 50%.

Experiments in Conscious Dogs

Mongrel dogs of either sex weighing 15-36 kg were chronically instrumented to monitor peak systolic pressure, heart rate, left ventricular pressure and its first derivative, LVdP/dt at 60 mm of mercury. Under halothane-nitrous oxide anesthesia, a precalibrated Konigsberg P22 Pressure Transducer was implanted into the left ventricle through a stab wound at the apex. Following recovery from surgery, a minimum of two weeks was allowed to train the dogs to lie quietly for four-hour periods. This conditioning was necessary to obtain stable, reproducible results from day to day. Dogs were fasted eighteen hours before an experiment. Gross behavioral observations of animals were made throughout each study. Compounds or placebo (lactose) were administered in gelatin capsules. The maximum effects on contractility at various dose levels were determined and plotted and the dose required to produce a 50-percent increase in contractility (ED$_{50}$) was determined by interpolation. The ED$_{50}$ for the compound of Example 1 was determined to be 50 mcg/kg.

The compounds of this invention may be administered by various routes including the oral, rectal, transdermal, subcutaneous, intravenous, intramuscular, or intranasal routes. It is a special feature of these compounds that they are effective positive inotropic agents, vasodilators, or bronchodilators following oral administration. The compounds are usually employed in the form of pharmaceutical compositions. Such compositions are prepared in a manner well known in the pharmaceutical art and comprise at least one active compound of the invention. Accordingly, the invention includes a pharmaceutical composition comprising as active ingredient a compound of Formula I associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The compositions usually contain as active ingredient from about 1% to about 95% by weight of a compound of the invention and are preferably formulated in a unit dosage form, each dosage containing from about 0.5 to about 500 mg, more usually 1 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range and typical dosages per day will normally fall within the range of about 0.020 to about 300 mg/kg of body weight. In the treatment of adult humans, a range of from about 0.020 to about 50 mg/kg, in single or divided doses, is preferred. However, it will be understood that the amount of the compound actually administered will be determined by a physician in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active ingedients any of the pharmaceutical compounds of the invention. The examples are illustrative only and are not intended to limit the scope of the invention in any way.

EXAMPLE 5

Hard gelatin capsules are prepared using the wing ingredients:

| | Quantity (mg/capsule) |
|---|---|
| 1',2'-dihydro-5'-(1,4,5,6-tetrahydro-6-oxo-3-pyridazinyl)spiro[cyclopropane-1,3'-(3H)-indole] | 250 |
| Starch dried | 200 |
| Magnesium stearate | 10 |

The above ingredients are mixed and filled into hard gelatin capsules in 460 mg quantities.

EXAMPLE 6

A tablet formula is prepared using the ingredients below:

| | Quantity (mg/tablet) |
|---|---|
| 1',4'-dihydro-6'-(1,4,5,6-tetrahydro-4-methyl-6-oxo-3-pyridazinyl)spiro[cyclobutane-1,3'(2'H)-quinoline] | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 7

An aerosol solution is prepared containing the following components:

| | Weight % |
|---|---|
| 1',4'-dihydro-6'-(1,4,5,6-tetrahydro-6-oxo-3-pyridazinyl)spiro[cyclopentane-1,3'(2'H)-quinolin]-2'-one | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remaining amount of propellant. The valve units are then fitted to the container.

EXAMPLE 8

Tablets each containing 60 mg of active ingredient are made up as follows:

| | |
|---|---|
| 1-butyl-1,5-dihydro-7-(1,4,5,6-tetrahydro-4-methyl-6-oxo-3-pyridazinyl)spiro[4H-1-benzazepine-4,1'-cyclopropan]-2(3H)-one | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 9

Capsules each containing 80 mg of medicament are made as follows:

| | |
|---|---|
| 1-ethyl-1,2,3,4-tetrahydro-7-(1,4,5,6-tetrahydro-4,4-diethyl-6-oxo-3-pyridazinyl)spiro[5H-1-benzazepine-5,1'-cyclobutane] | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 10

Suppositories each containing 225 mg of active ingredient are made as follows:

| | |
|---|---|
| 2',3'-dihydro-1'-t-butyl-6'-(1,6-dihydro-4-isopropyl-6-oxo-3-pyridazinyl)spiro[cyclopropane-1,4'(1'H)-quinolin]-2'-one | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 11

Suspensions each containing 50 mg of medicament per 5 ml dose are made as follows:

| | |
|---|---|
| 1,2,4,5-tetrahydro-7-(1,4,5,6-tetrahydro-1,4-dimethyl-6-oxo-3-pyridazinyl)spiro[3H-1-benzazepine-3,1'-cyclopentane] | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl-

I claim:
1. A compound of the formula

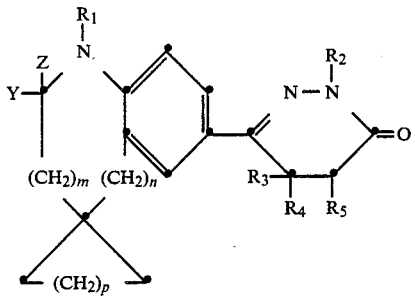

wherein
Y and Z are each hydrogen, or when taken together are =O;
$R_1$, $R_2$, $R_3$, $R_4$, and $R_5$ are independently hydrogen or $C_1$–$C_4$ alkyl, or $R_5$ and one of $R_3$ and $R_4$ taken together form a bond;
m and n are independently 0, 1 or 2, provided that (m+n) is no greater than 2; and
p is 0, 1 or 2, and pharmaceutically acceptable acid addition salts thereof.

2. A compound according to claim 1 wherein Y and Z taken together are =O.

3. A compound according to claim 2 wherein each of $R_1$, $R_2$, and $R_3$ is hydrogen.

4. A compound according to claim 3 wherein m and n are each 0.

5. A compound according to claim 4 wherein $R_4$ is hydrogen.

6. The compound of claim 5 which is 5'-(1,4,5,6-tetrahydro-6-oxo-3-pyridazinyl)spiro[cyclopropane-1,3'-(3H)indol]-2'(1'H)-one or a pharmaceutically acceptable salt thereof.

7. A compound according to claim 4 wherein $R_4$ is methyl.

8. The compound of claim 7 which is 5'-(1,4,5,6-tetrahydro-4-methyl-6-oxo-3-pyridazinyl)spiro[cyclopropane-1,3'-(3H)indol]-2'(1'H)-one or a pharmaceutically acceptable salt thereof.

9. A method of treating a mammal, including a human subject, suffering from or susceptible to heart failure, which comprises administering to said mammal an effective amount of a compound of claim 1.

10. The method according to claim 9 employing a compound wherein Y and Z taken together are =O.

11. The method of claim 10 employing 5'-(1,4,5,6-tetrahydro-6-oxo-3-pyridazinyl)spiro[cyclopropane-1,3'-(3H)indol]-2'(1'H)-one or a pharmaceutically acceptable salt thereof.

12. The method of claim 10 employing 5'-(1,4,5,6-tetrahydro-4-methyl-6-oxo-3-pyridazinyl)spiro[cyclopropane-1,3'-(3H)indol]-2'(1'H)-one or a pharmaceutically acceptable salt thereof.

13. A pharmaceutical formulation which comprises a compound of claim 1 in association with a pharmaceutical carrier.

14. A formulation according to claim 13 employing a compound wherein Y and Z taken together are =O.

15. A formulation according to claim 14 employing a compound wherein each of $R_1$, $R_2$, and $R_3$ is hydrogen.

16. A formulation according to claim 15 employing a compound wherein m and n are each 0.

17. A formulation according to claim 16 employing a compound wherein $R_4$ is hydrogen.

18. A formulation according to claim 17 employing 5'-(1,4,5,6-tetrahydro-6-oxo-3-pyridazinyl)-spiro[cyclopropane-1,3'-(3H)indol]-2'(1'H)-one or a pharmaceutically acceptable salt thereof.

19. A formulation according to claim 16 employing a compound wherein $R_4$ is methyl.

20. A formulation according to claim 19 employing 5-(1,4,5,6-tetrahydro-4-methyl-6-oxo-3-pyridazinyl)-spiro[cyclopropane-1,3'-(3H)indol]-2'(1'H)-one or a pharmaceutically acceptable salt thereof.

* * * * *